United States Patent [19]

Michaeli

[11] Patent Number: 4,912,093

[45] Date of Patent: Mar. 27, 1990

[54] USE OF SYNTHETIC SULFATED SACCHARIDES TO ENHANCE WOUND HEALING

[75] Inventor: Dov Michaeli, San Francisco, Calif.

[73] Assignee: Marion Laboratories, Inc., Kansas City, Mo.

[21] Appl. No.: 922,358

[22] Filed: Oct. 23, 1986

Related U.S. Application Data

[63] Continuation-in-part of Ser. No. 914,192, Oct. 1, 1986, abandoned, which is a continuation-in-part of Ser. No. 813,243, Dec. 24, 1985, abandoned.

[51] Int. Cl.$^4$ ............................................. A61K 31/70
[52] U.S. Cl. ........................................ 514/53; 514/23; 514/54; 514/21
[58] Field of Search ......................... 514/53, 21, 54, 23

[56] References Cited

U.S. PATENT DOCUMENTS

| | | | |
|---|---|---|---|
| 4,357,732 | 1/1983 | Poulsen et al. | 128/156 |
| 4,533,549 | 8/1985 | Lasker | 536/21 |
| 4,581,221 | 4/1986 | Kuperus | 424/1.1 |

FOREIGN PATENT DOCUMENTS 0093850  4/1975  Japan ...................................... 514/53

*Primary Examiner*—Johnnie R. Brown
*Assistant Examiner*—Elli Peselev
*Attorney, Agent, or Firm*—Theresa M. Gillis

[57] ABSTRACT

The use of sulfated oligosaccharides, particularly mono- and disaccharides, and their salts to enhance healing of wounds is described. Preferred saccharides are those having three or more sulfate groups, with persulfation being most preferred. Preferred salts are the soluble salts most preferably the alkali metal salts, particularly potassium and sodium salts. Sucrose octosulfate is the most preferred material. The saccharides may be used in any form, including liquids, gels or time release polymers. In preferred practice the saccharide is used in combination with collagen. Wounds, in particular those ocurring in the skin and bone tissues, may be treated with the compositions. Wound healing is promoted even in wounds, such as decubitis ulcers, which are commonly resistent to the natural healing process.

21 Claims, No Drawings

USE OF SYNTHETIC SULFATED SACCHARIDES TO ENHANCE WOUND HEALING

This application is a continuation-in-part of copending application Ser. No. 06/914,192 filed Oct. 1, 1986 now abandoned which is a continuation of application Ser. No. 06/813,243 filed Dec. 24, 1985, now abandoned.

FIELD OF THE INVENTION

This invention relates to the use of sulfated saccharides, preferably mono- and disaccharides, and most preferably sucrose octasulfate or its salts, as agents for the enhancement of healing of wounds in collagen containing tissues, including skin and bone.

BACKGROUND OF THE INVENTION

The skin forms a barrier between the body and the environment, with one of its principal functions being the protection of the body from invasion by potentially hazardous materials and organisms. The skin's integrity is therefore all important to the continued well-being of the individual, and any breach or rupture represents a threat that must be met by the body in order to protect its continued existence.

Under normal circumstances the body provides mechanisms for healing a rupture or breach to restore the integrity of the skin barrier. The repair process for even minor breaches or ruptures takes a period of time extending from hours and days to weeks; and in some instances, as in ulceration, the breach or rupture may persist for extended periods of time, i.e., months or even years. At all times, whether brief or extended, the potential for invasion by pathogenic organisms or foreign substances continues until new tissue has been generated to fully close the rupture or breach.

The healing process is brought about by complex biological mechanisms generally involving several groups of special cells and proteins. Leukocytes, such as neutrophils and macrophages, crowd the wound site and digest foreign pathogens and debris. Such cells also send out chemical signals that marshal fibroblasts in the wound vicinity and ultimately generate connective structures, principally, collagen, which make up a major portion of the new tissues. Endothelial cells generate new blood capillaries that grow into the reconstructed tissue areas where their presence is necessary to supply nutrients to the newly growing tissue cells and remove catabolic products. As the new capillaries grow, the cells on the margin of the wound simultaneously multiply and grow inwardly. The fibrous tissue arising from this cell growth eventually fills the wound cavity with a network of interlacing threads of collagen which in due time, arrange themselves in firm bands and form the permanent new tissue.

The surface of the wound subsequently is covered by a process of enlargement, flattening, and multiplication of the surface, or epithelial cells at the wounds' edge. These epithelial cells spread as sheets into the wound, beneath the scab. Eventually the proliferating epithelial cell sheets emanating from the wound sides coalesce to cover and close the wound on the outer surface.

All of the above noted healing processes take considerable time. The rate of healing is influenced by the wound's freedom from infection, the general health of the individual, presence of foreign bodies, or the like. Even for healthy individuals with no complications, healing can take a considerable period of time, i.e., days to weeks. In some instances, the healing process can be impaired by constitutional deficiencies, or by disease processes, and healing may never effectively take place.

Until such time as at least superficial healing has occurred, the individual remains at risk from continued or new infection. Therefore there is a time/rate related risk factor attendant to all wound situations. The quicker the wound can heal, the sooner the risk is removed. Thus any procedure that can influence the rate of wound healing or favorably influence healing of intractible wounds would be of great value.

SUMMARY OF THE INVENTION

This invention relates to the use of synthetic polysulfated saccharides, in particular mono-, di-, tri- and tetrasaccharides (herein collectively termed "oligosaccharides") and their pharmaceutically acceptable salts to enhance wound healing in tissues having a collagen matrix, such as skin and bone. The invention has particular reference to use of mono- and disaccharides having three or more sulfate groups. The persulfated mono- and disaccharides are believed to be particularly useful in wound healing, with the most preferred being the persulfated disaccharide, sucrose octasulfate, optimally potassium sucrose octasulfate.

More particularly this invention provides polysulfated oligosaccharide compositions which, upon topical application to the wound, promote wound healing by attracting repair cells to the wound site. The oligosaccharide may be applied to the wound in a number of ways including as a collagen composite, in liquid form as for example in an aqueous solution or suspension, or encapsulated in slow release polymers. The preferred composition of the invention contains a polysulfated disaccharide in water or an isotonic salt solution, preferably in combination with collagen. The most preferred compositions contain 7 to 10 mg/ml collagen and 0.1 to 1.0 mg/ml potassium sucrose octasulfate suspended in phosphate buffered saline.

DETAILED DESCRIPTION OF THE INVENTION

This invention provides methods and compositions for enhancing wound healing in body tissues having a collagen matrix. Wound healing as used herein includes healing of skin and bone wounds caused by disease, trauma or any other means. It has particular reference to skin ulcers, such as decubitus ulcers or venous stasis ulcers as well as other wounds wherein the body's natural healing process fails. The mechanism by which the compositions operate is believed to involve stimulation of migration of repair cells, such as fibroblasts into the wound site. Both a wound's ability to heal and the rate of healing are believed to be favorably affected by the compositions.

The efficacy of the compositions enhancing wound healing was surprising in view of the fact that sucralfate, a commercial product sold for gastrointestinal ulcer treatment has properties making it undesirable for wound healing. Where sucralfate is applied to a wound, only angiogenesis secondary to the inflammatory effect of the compound is observed. Wound healing with neovascularization and fibroblast (rather than macrophage) migration was not observed with sucralfate. In view of sucralfate's properties, production of such wound healing effects including revascularization and fibroblast migration with the compositions of the invention was indeed surprising.

The compositions of the invention contain polysulfated oligosaccharides (herein having particular reference to mono-, di-, tri- and tetrasaccharides) or their salts. The oligosaccharides useful in the compositions of the invention preferably contain sugar units which naturally occur in the human metabolism. Preferred oligosaccharides are mono- and disaccharides. Of such saccharides those having three or more sulfate groups exhibit significant wound healing effects in tests using wound healing models. Persulfation appears to result in greatest wound healing efficacy. Most preferably the compositions of the invention contain a persulfated dissaccharide, optimally sucrose octasulfate (SOS). The pharmaceutically acceptable salts of the oligosaccharides are included within the scope of the invention. Alkali metal salts such as potassium and sodium salts are particularly preferred. Use of salts which cause angiogenesis secondary to inflammation should be avoided. It is believed that soluble salts are required for optimal wound healing.

The oligosaccharide is applied to a skin wound in an effective amount which minimizes hemorrhagic response or inflammation. It may be applied in a liquid form, such as a solution of water or an isotonic salt solution, as an aqueous gel dispersion, or in a polymer matrix from which it is released after application. Optimally it may be applied in combination with collagen.

The oligosaccharide is applied in combination with a pharmaceutically acceptable carrier. Commonly an isotonic salt solution, such as phosphate buffered saline (PBS), is used as the vehicle for the oligosaccharide. The oligosaccharide may be present in the solution at concentrations of about 0.1 mg/ml to 10.0 mg/ml. However, levels of about 0.1 mg/ml to 1.0 mg/ml are preferred in order to insure sufficient oligosaccharide to stimulate wound repair while avoiding an excess of oligosaccharide which may cause local hemorrhage or inflammation at the wound site. A more preferred range is about 0.25 to 0.35 mg/ml. With potassium sucrose octasulfate levels of about 0.28 mg/ml have been found optimal.

The oligosaccharide may be applied to the wound in combination with collagen. To form a collagen and oligosaccharide composite, the oligosaccharide and collagen may be suspended in solution. In preferred practice the collagen is present in the composite at levels of about 1 to 15 mg/ml, more preferably 7 to 10 mg/ml, and most preferably at 8.75 mg/ml levels. At too high levels inhibition of fibroblast cell migration occurs.

The collagen may be pure natural collagen isolated from mammalian sources by removal of extraneous proteinaceous materials. However, the collagen used is preferably collagen having reduced antigenicity due to enzymatic cleavage of peptide ends of natural collagen.

Reduced antigenic, enzyme-treated collagen is an article of commerce. It can be secured from the Collagen Corporation of Palo Alto, Calif. under the trademarked name "Zyderm." Although such purified collagen is preferred in the present compositions, for purposes of this invention it is only necessary that the collagen be prepared in a form suitable for human use. One preferred form is a collagen in sterile condition in an aqueous suspension. Some inclusion of materials commonly associated with collagen, e.g., polysaccharides, can be tolerated and does not interfere with the benefits of the wound healing compositions.

Preferably the collagen and oligosaccharide levels are directly proportional. That is with higher concentration of oligosaccharide more collagen is used. Preferably the collagen is 25 to 35 times the concentration of the oligosaccharide.

The composites may be prepared from dispersions of the individual components. Collagen is available as a saline suspension at a concentration of 35 mg/ml. The commercial product is diluted with sterile normal saline to the concentration levels noted above, e.g., 8.75 mg/ml. Sucrose octasulfate solution is added with good mixing to the diluted collagen suspension to achieve the desired level, e.g. 0.28 mg/ml.

For some purposes it may be desirable to thicken the compositions of the invention into a more viscous or semi-solid gelled state. If such is desired, standard medically acceptable gelling materials, e.g. cellulose, may be included in the compositions. It is also possible to add small amounts of an antibiotic (e.g. neomycin sulfate, silver sulfadiazine) normally used for topical applications. A topical antibiotic is not necessary to promote wound healing by the present compositions, but rather is added solely as a matter of convenience in the general management of wounds.

The prepared compositions should be maintained under refrigeration; but should not he frozen or maintained at room temperature. Freezing will interfere with suspension properties. Ambient temperatures may permit the growth of any minute amount of contaminants as well as cause changes in the fibrillar structure of collagen.

The wound healing compositions are placed in direct contact with the wound. (When used herein application to a wound means directly contacting the wound with the composition. Typically the direct contact with the wound occurs immediately at the time the patient is treated rather than subsequently as a result of body functions, such as digestion or circulatory functions, later resulting in contact with a wound.) The compositions may be used as follows. The wound is first thoroughly cleansed and decontaminated according to standard medical practice and any necrotic tissue is debrided to leave as clean and sterile a wound surface as possible. A quantity of the oligosaccharide or oligosaccharide-collagen suspension or composite is applied liberally to all surfaces of the wound. A gauze dressing, thoroughly moistened with the suspension, is placed over the wound. From time to time, e.g., once or twice a day, the dressing is removed and the wound surfaces are cleaned according to standard medical practice. The wound healing composition is then reapplied to the wound surfaces, and the wound is covered with new moist gauze dressings as noted above. This procedure is generally followed until the healing process is complete, that is, until new epithelial tissue completely closes the wound surface, at which time, application of the wound healing composition is discontinued. The wound healing composition may be applied by other suitable means as well.

In addition to aiding skin healing, the wound healing compositions of the invention may also be used to promote bone healing. Because of their healing effects, the compositions are believed to be suitable for use in or as prosthetic devices, for treatment of periodontal disease and in artificial skins. It is to be understood that application of the wound healing benefits of the compositions to both human and veterinary medicine is contemplated by this invention.

The oligosaccharide is believed to promote vascularization of the wound, to attract fibroblasts and endothelial cells by chemotaxis and to provide an environment favorable to cells which participate in the healing process. The experiments described in the examples below demonstrate the biological activity of sucrose octasulfate in enhancement of wound repair. They also suggest the mechanisms that may underlie this effect.

EXAMPLES

Example 1

Preparation of Potassium Sucrose Octasulfate

Pyridine sulfur trioxide (359.70 g, 2.26 mole) was slurried in 1800 ml of the pyridine, heated to 45° C., and sucrose (95.84 g, 0.28 mole) was added. The reaction mixture was heated to 65° C. and maintained at this temperature for 4 hours. After cooling, the pyridine was decanted, the solid was dissolved in deionized water, methanol was added and the pH was raised to 8–9 by addition of 20% KOH. The white precipitate was collected, dried, and recrystallized from deionized water/methanol to provide 195.0 g (52.6% yield) of white, granular crystals, melting point 143°–147° C. with decomposition.

Example 2

Synthesis of Potassium Sucrose Octasulfate

The following is a preferred method of synthesizing sucrose octasulfate. In a flame-dried 12-liter three-necked distilling flask were combined pyridine (5000 ml) and pyridine sulfur trioxide (989.23 g, 6.22 mol). With stirring, sucrose (265.96 g, 0.77 mol) was carefully added. The reaction mixture was heated to 65° C. and maintained at that temperature for 4 hours. As the reaction progressed, the product separated as a thick oil. While the reaction mixture was still hot, the pyridine was decanted and the residue dissolved in a deionized water (2500 ml). With stirring, the solution was cooled in an ice bath and the pH was adjusted to 8–9 by the careful addition of 20% aqueous KOH. Completion of precipitation of the product was accomplished by the slow addition of methanol (5000 ml). The solid was filtered and washed with 1:1 deionized water/methanol (2000 ml) followed by methanol (2000 ml). The wet filter cake was dried at 45° C. under vacuum for 15 hours.

The crude product was dissolved at 45° C. in deionized water (2700 ml), the pH adjusted to 9.7 with 10% aqueous KOH, the solution filtered hot through filter aid, and the product allowed to precipitate while stirring with cooling with an ice bath. The precipitate was collected, washed with 1:1 deionized water/methanol (2000 ml) and methanol (2000 ml), and dried at ambient temperature under vacuum for 15 hours. The solid was recrystallized four additional times as above to provide 453.2 g (45.3%) of potassium sucrose octasulfate as white crystals, mp 146°–152° C. (dec.). HPLC assay (30 cm μBondapak $NH_2$; 1 M ammonium sulfate, pH 3.5 mobile phase; 1 ml/min flow rate; 0.25 cm/min chart speed; 8× attenuation refractometer; refractometer temperature 30° C.; column temperature 30° C.) showed the product to contain 98.6% potassium sucrose octasulfate with the remainder being lower sulfated species of sucrose. $^1HNMR$ shifts in ppm from TMS: 4.26–4.55 (10H,m); 4.77–4.88 (2H,m); 5.17 (1H,d); 5.80 (1H,d). $^{13}CNMR$ shifts in ppm from TMS: 66.3 ($CH_2$); 66.4 ($CH_2$); 68.3 ($CH_2$); 69.5 (CH); 73.7 (CH); 74.2 (CH); 75.6 (CH); 79.0 (CH); 79.3 (CH); 79.3 (CH); 90.4 (CH); 103 1 (C). Elemental Analyses (Calculated,Found): C (11.19, 10.91); H (1.10, 1.60); S (19.92, 18.56); K (23.70, 23.67).

Example 3

Synthesis of Potassium Sucrose Penta/Hexasulfate Mixture

In like manner to that described for the synthesis of potassium sucrose octasulfate, a mixture of potassium sucrose penta- and hexasulfate was synthesized from sucrose (17.12 g, 0.05 mol) and pyridine sulfur trioxide (19.90 g, 0.125 mol) in pyridine (300 ml). The product thus obtained was dissolved in deionized water, filtered through filter aid, diluted with an equal volume of methanol, and stirred for 20 minutes with cooling with an ice bath. The precipitate was filtered, washed with methanol and dried at 50° C. under vacuum for 3 hours to provide the penta/hexa mixture as a white solid, mp 209 210.5C (dec.). HPLC assay, as for potassium sucrose octasulfate, showed the product to contain 45% potassium sucrose hexasulfate and 45% potassium sucrose pentasulfate, with the remainder being sucrose tri-, tetra- and heptasulfates.

Example 4

Synthesis of Potassium Sucrose Trisulfate

In a three-necked 5-liter distilling flask (dried at 110° C. for 1 hour) were combined with stirring trityl chloride (423.0 g, 1.52 mol), pyridine (1800 ml), and sucrose (153 g, 0.45 mol). After stirring at ambient temperature for 60 hours, acetic anhydride (657 g, 6.44 mol) was added, stirring was continued for 1 hour, and then the flask was placed in a refrigerator overnight. The solid which formed was removed by filtration and the filtrate was poured into ice water (18 l), stirred for 30 minutes, and the solid which formed was filtered and washed with deionized water. The wet filter cake was slurried in methanol (4 l) for 30 minutes, filtered, washed with methanol, and dried at 45° C. under vacuum for 15 hours. The crude solid was recrystallized by dissolving in THF (800 ml), filtering to remove insolubles, and diluting the filtrate with methanol. After standing in a refrigerator overnight, the precipitate which formed was filtered, washed with methanol, and dried at 40° C. under vacuum for 18 hours to provide 324 g (56.6%) of tri-O-trityl-penta-O-acetylsucrose as white, granular crystals, mp 232°–233.5° C. The compound showed one spot on TLC (1:1 dichloromethane:toluene, Rf=0.04; 2:1 ether:toluene Rf=0.79).

In a three-necked 2-liter distilling flask were combined with stirring tri-O-trityl-penta-O-acetylsucrose (60.0 g, 0.047 mol) and acetic acid (1500 ml). The reaction mixture was heated to reflux and deionized water (30 ml) was added. After 30 minutes at reflux, the reaction mixture was allowed to cool to ambient temperature, and the acetic acid was evaporated to low volume under reduced pressure. The crystals of triphenylmethanol which formed were filtered and rinsed with acetic acid, and the filtrate was evaporated under high vacuum to provide a tacky solid which was dissolved in dichloromethane and chromatographed on silica gel. Elution with 2:1 ether:toluene removed the remaining triphenylmethanol and the silica gel was slurried in methanol to obtain the product. Removal of the methanol followed by recrystallization from dichloromethane/petroleum ether provided 6.02 g (21.9%) of penta-O-acetylsucrose as white, granular crystals, mp 153°–155° C. The product showed one spot on TLC (2:1 ether:toluene, Rf=0.05 using $H_2SO_4$ spray).

In a 500 ml distilling flask (dried at 110° C. for 3 hours) were combined dry pyridine (90 ml), penta-O-acetylsucrose (7.59 g, 0.013 mol), and pyridine sulfur trioxide (14.31 g, 0.09 mol). The reaction mixture was stirred overnight at ambient temperature, diluted with deionized water (210 ml), and barium hydroxide solution was added until the pH was 8.00. The barium sulfate which formed was removed by filtration and the filtrate was evaporated to dryness. The pale yellow solid which resulted was dried at 10° C. under vacuum for 1.5 hours to provide 10.21 g (77%) of barium penta-O-acetylsucrose trisulfate as an off-white, granular solid. The IR of the solid was consistent.

In a 500 ml distilling flask were combined with stirring barium penta-O-acetylsucrose trisulfate (10.21 g, 0.01 mol) and methanol (250 ml) which had been passed through a column packed with alumina. The mixture was cooled with an ice bath and ammonia gas was added for 4 hours, keeping the reaction temperature near 10° C. The reaction mixture was then allowed to warm to ambient temperature and stirred overnight. The solid which formed was filtered, rinsed with alumina-treated methanol, and dried at 50° C. under vacuum for 1 hour to provide 5.98 g (74%) of barium sucrose trisulfate as a granular, off-white solid. The IR showed no carbonyl band.

Only high-purity water was used for this reaction. Approximately 35 g of Amberlite IR 120 H+resin was slurried for 20 minutes in 1 N potassium hydroxide solution (200 ml), most of the liquid was decanted, and the resin was placed in a 450 mm×15 mm glass column with sintered glass support. The resin was washed with water until the pH was near 7. In 150 ml of water was slurried barium sucrose trisulfate (8.31 g, 0.01 mol), insoluble solids were removed by filtration, and the filtrate was passed down the column at a moderate rate of flow. The column was rinsed with water (100 ml) and the eluents were combined, the water was evaporated under reduced pressure, and the resulting off-white solid was dried in a desiccator over $CaCl_2$ at ambient temperature under vacuum for 1 hour to provide 5.91 g (85%) of potassium sucrose trisulfate, mp 215° C. (dec.). $^1H$ NMR shifts in ppm from TMS: 3.62–3.68 (1H,m); 3.87 (2H,s); 3.92–3.99 (2H,m); 4.07–4.31 (8H,m); 5.64 (1H,d). $^{13}C$ NMR shifts in ppm from TMS: 61.8 ($CH_2$); 68.0 ($CH_2$); 70.7 ($CH_2$); 72.6 (CH); 72.7 (CH); 73.0 (CH); 75.5 (CH); 77.8 (CH); 78.5 (CH); 81.0 (CH); 94.1 (CH); 104.4 (C). Elemental Analyses (Calculated,-Found): C (20.69,20.98); H (2.75,2.83); S (13.80,13.04); K (16.84,15.93).

Example 5

Synthesis of Potassium β-Lactose Octasulfate

In like manner to that described for the synthesis of potassium sucrose octasulfate, potassium β-lactose octasulfate was synthesized from β-lactose (27.7 g, 0.078 mol) and pyridine sulfur trioxide (105.5 g, 0.663 mol) in pyridine (530 ml). The solid thus prepared was recrystallized three times in the following manner: the solid was dissolved in a minimal amount of deionized water, the pH was adjusted to 9–10 by addition of dilute aqueous KOH, and the solution was cooled with an ice bath. The solid which separated was isolated by filtration, washed with 1:1 methanol/water, and dried in a desiccator over $CaCl_2$ at ambient temperature under vacuum for 15 hours to provide potassium β-lactose octasulfate as a white solid, mp 147°–152° C. (dec.), in 3.6% yield. HPLC assay as for potassium sucrose octasulfate showed the product to contain 91.5% potassium β-lactose octasulfate with the remainder being lower sulfated species of β-lactose. $^1HNMR$ shifts in ppm from TMS: 3.91 (1H,m); 4.04 (2H,m); 4.16–4.29 (4H,m); 4.39.4.46 (4H,m); 4.73 (1H); 4.98 (1H,s); 5.45 (1H,d). $^{14}CNMR$ shifts in ppm from TMS: 64.7 ($CH_2$); 66.3 ($CH_2$); 71.0 (CH); 72.1; (CH); 74.4 (CH); 74.5 (CH); 74.8 (CH); 74.8 (CH); 74.8 (CH); 76.3 (CH); 95.6 (CH); 100.3 (CH). Elemental analyses (Calculated, Found): C (11.19,11.38); H (1.10,1.31); S (19.92,19.73); K (24.29,23.25).

Example 6

Synthesis of Potassium Maltose Octasulfate

In like manner to that described for the synthesis of potassium sucrose octasulfate, potassium maltose octasulfate was synthesized from maltose (26.70 g, 0.074 mol) and pyridine sulfur trioxide (105.5 g, 0.663 mol) in pyridine (530 ml). The solid thus obtained was recrystallized in the following manner: the solid was dissolved in a minimal amount of deionized water at 30° C. and a small amount of methanol was added; the solid which formed was isolated by filtration and the filtrate was refrigerated to obtain a second crop; the solids were combined and the procedure repeated until adequate purity was achieved. After drying in a desiccator over $CaCl_2$ at ambient temperature under vacuum for 15 hours, this provided potassium maltose octasulfate as a white solid, mp 140–148° C. (dec.), in 4% yield. HPLC assay as for potassium sucrose octasulfate showed the product to contain 78.3% potassium maltose octasulfate with the remainder being lower sulfated species of maltose. Elemental Analyses (Calculated, Found): C (11.19,11.38); H (1.10,1.41); S (19.92,19.46); K (24.29,23.24).

Example 7

Synthesis of Potassium Trehalose Octasulfate

In like manner to that described for the synthesis of potassium sucrose octasulfate, potassium trehalose octasulfate was synthesized from trehalose (30.64 g, 0.081 mol) and pyridine sulfur trioxide (110.0 g, 0.691 mol) in pyridine (550 ml). The solid thus obtained was recrystallized twice by dissolving at 40° C. in a minimal amount of deionized water, then cooling in an ice bath. After drying in a desiccator over $CaCl_2$ at ambient temperature under vacuum for 15 hours, this provided potassium maltose octasulfate as a white solid, mp 160°–166° C. (dec.), in 12.5% yield. HPLC assay as for potassium sucrose octasulfate showed the product to contain 91.5% potassium trehalose octasulsulfate with the remainder being lower sulfated species of trehalose. $^1H$ NMR shifts in ppm from TMS: 4.35–4.49 (6H,m); 4.56–4.66 (4H,m) 4.93 (2H,t); 5.67 (2H,d). $^{13}C$ NMR shifts in ppm form TMS: 65.7 ($CH_2$); 68.6 (CH); 73.2 (CH); 74.1 (CH); 75.6 (CH); 91.7 (CH). Elemental Analyses (Calculated, Found); C (11.19,11.04); H (1.10,1.53); S (19.92,19.26); K (24.29,22.26).

Example 8

Synthesis of Potassium Glucose Pentasulfate

In like manner to that described for the synthesis of potassium sucrose octasulfate, potassium glucose pentasulfate was synthesized from glucose (11.71 g, 0.065 mol) and pyridine sulfur trioxide (51.6 g, 0.324 mol) in pyridine (250 ml). The product thus obtained was recrystallized eight times in the following manner: the solid was dissolved in deionized water, the pH was adjusted to 9.8 with 10% aqueous KOH, the solution was filtered warm through filter aid, and methanol was added until the solution was faintly cloudy; after cooling in an ice bath with stirring, the solid which separated was collected, washed with methanol and dried at ambient temperature under vacuum for 15 hours. This provided 2.4 g (4.8%) of potassium glucose pentasulfate as a white solid, mp 110°–135° C. (dec.). HPLC assay as for potassium sucrose octasulfate showed the product to contain 96% potassium glucose pentasulfate with the remainder being lower sulfated species of glucose. HNMR shifts in ppm from TMS: 4.23–4.30 (2H,m); 4.52–4.61 (3H,m); 4.81 (1H,t); 5.62 (1H,d). $^{13}$CNMR shifts in ppm from TMS: 7.5 ($CH_2$); 71.9 (CH); 73.5 (CH); 74.4 (CH); 74.9 (CH); 96.3 (CH). Elemental Analyses (Calculated,Found): C (9.35,9.32); H (0.92,0.78); S (20.79,20.68); K (25.36,25.59).

Example 9

Synthesis of Potassium Mannose Pentasulfate

In like manner to that described for the synthesis of potassium sucrose octafulfate, potassium mannose pentasulfate was synthesized from mannose (46.6 g, 0.259 mol) and pyridine sulfur trioxide (206.1 g, 1.298 mol) in pyridine (1000 ml). The product thus obtained was recrystallized three times in the same manner as used for potassium glucose pentasulfate to provide 40.3 g (20.2%) of potassium mannose pentasulfate as an off-white solid, mp 168°–173° C. (dec.). HPLC assay as for potassium sucrose octasulfate showed the product to contain 88.3% potassium mannose pentasulfate with the remainder being lower sulfated species of mannose. $^1$H NMR shifts in ppm from TMS: 4.174.22 (2H,m); 4.30–4.49 (2H,m): 4.64–4.68 (1H,m): 4.89–4.90 (1H,m); 5.87 (1H,d). $^{13}$CNMR shifts in ppm from TMS: 67.1 ($CH_2$); 71.5 (CH); 71.6 (CH); 73.8 (CH); 75.2 (CH); 96.0 (CH). Elemental Analyses (Calculated,Found): C (9.35,9.50); H (0.92,1.23); S (20.79,20.28); K (25.36,23.86).

Example 10

Synthesis of Potassium Melezitose Persulfate

In like manner to that described for the synthesis of potassium sucrose octafulfate, potassium melezitose persulfate was synthesized from melezitose(50.00 g, 0.096 mol) and pyridine sulfur trioxide (175.08 g, 1.10 mol) in pyridine (1225 ml). The product thus obtained was recrystallized twice in the same manner as used for potassium maltose octasulfate. This provided the product as a white solid, mp 151°–157° C. (dec.) in 3.7% yield. HPLC assay as for potassium sucrose octasulfate showed the product to contain 92.5% potassium melezitose nonasulfate with the remainder being higher and lower sulfated species of melezitose. Elemental Analyses (Calculated,Found): C (11.98,12.60); H (1.17,1.45); S (19.55,19.12); K (23.84,22.43).

Example 11

Synthesis of Potassium Stachyose Persulfate

In like manner to that described for the synthesis of potassium sucrose octafulfate, potassium stachyose persulfate was synthesized from stachyose (30.00 g, 0.041 mol) and pyridine sulfur trioxide (92.09 g, 0.579 mol) in pyridine (960 ml). The product thus obtained was recrystallized three times in the same manner as used for potassium maltose octasulfate. This provided the product as a white solid, mp 146°–148° C. (dec.), in 4.4% yield. HPLC assay as for potassium sucrose octasulfate showed the product to contain a mixture of 15.9% potassium stachyose decasulfate, 13.8% undeca, 15.2% dideca, 32.4% trideca, and 22.7% tetradeca. Elemental Analyses (Calculated,Found): C (12.42,12.92); H (1 22,1.62); S (19.34,18.23); K (23.59,21.22).

Example 12

(a) Preparation of Collagen Potassion Sucrose Octasulfate Composite

Sucrose octasulfate made in accordance with Example 1 was dissolved in phosphate buffered saline and added to ZYDERM (Collagen Corp., Palo Alto, Calif.), a purified collagen having reduced antigenicity, to make a final concentration of 0.28 mg/ml sucrose octasulfate and 8.75 mg/ml collagen. All diluent solutions were passed through a 0.22 $\mu M$ polyvinylidene difluoride (PVDF) filter (Millipore, Bedford, Mass.). The composites were formed by passaging collagen and sucrose octasulfate between two syringes connected via a stopcock.

(b) Preparation of Sustained Release Microcapsules

Hydron (Hydron Corp., New Brunswick, N.J.), a polymer that allows the sustained release of macromolecules, was mixed with an equal volume of phosphate buffered saline containing 0.28 mg/ml potassium sucrose octasulfate or plain phosphate buffered saline. Twenty-1 aliquots were dropped onto a polyethylene sheet and dried under reduced pressure.

(c) Preparation of Sponge Implants

Ivalon (polyvinyl alcohol) sponges were cut into cylinders 4 mm in diameter and 6 mm in length. The cylinders were soaked in tap water for one hour, dried for an hour in an oven at 50 degrees Centigrade and weighed. Sponges weighing 6.5±0.4 mg were used. Before implantation they were washed extensively in distilled water, autoclaved in the presence of leucine, washed extensively in distilled water, auto-claved again and washed finally in sterile PBS. They were kept in sterile PBS at 4 degrees Centigrade until four hours before implantation, when the buffer temperature was allowed to reach room temperature.

Example 13

Effect of Collagen/Sucrose Octasulfate on Formation of Granulation Tissue

By mean of subcutaneous implantation of Ivalon sponges the phase of granulation tissue formation in the repair process can be evaluated. Following a vigorous cleanup procedure the sponge material evokes only minimal inflammatory response.

Thus, the granulation tissue invading the sponge interstices most likely represents a normal repair process rather than a granuloma formed in response to a foreign body. The relative paucity of acute and chronic inflammatory cells, and the lack of giant cells which are characteristic of a foreign body reaction during the tests described below supports this conclusion.

Implantation Procedure

Sterile sponges prepared as set forth in Example 12 were injected with a 50-μL suspension of collagen/sucrose octasulfate suspension prepared as in Example 12. The collagen concentration was 8.75 mg/ml while the sucrose octasulfate concentrations were 0.01, 0.2, 1.0 or 10 mg/ml. The sponges were surgically implanted into 350-500 g, male Sprague-Dawley rats. Before the implantation procedure three rats were anesthetized and their dorsal surfaces shaved and wiped with Predodyne (West Chemical Products, Lynbrook, N.Y.). Six 6-mm incisions were cut in groups of two (one on each side of the vertebral column rostrally, centrally and caudally), spaced equi-distant from each other between the pectoral and pelvic girdles on the dorsal surface. At each incision a pocket was made between the panniculus carnosus and the dermis and two sponges inserted into it, one rostrally and the other caudally; a total of 12 sponges were thus implanted in each animal. The position of each test preparation was alternated between the rostral, central and caudal positions to control the variation due to anatomical location. The incisions were closed with 11-mm Michel wound clips (Propper, Long Island City, N.Y.). Seven days following implantation the animals were sacrificed and the sponges surgically removed with their adhered connective tissue capsules. Controls, sponges injected with either PBS or collagen only were treated in a similar manner. In all, approximately 120 sponges per group were used in the study and randomly selected for biochemical and histologic analysis.

Histological Analysis

The sponges were fixed in formalin and embedded in either plastic or Paraplast following dehydration. Sections were stained with hematoxylin and eosin, trichrome, silver or PAS. A scale of 0-4+ (integers only being assigned by an individual observer) was used in blind fashion by four independent observers to qualitatively record the degree of inflammatory response and mesenchymal cell infiltration inside the sponge. For inflammation the zero rank exhibited no leukocytes, lymphocytes or giant cells, while the rank of 4+ displayed extensive leukocyte infiltration, necrotic cell debris and giant cells. Mesenchymal cell infiltration was also scored on a predetermined scale from 0-4. Zero response showed few if any undifferentiated fibroblasts, migrating endothelial cells and histiocytes which could not be differentiated from other migrating mesenchymal cells, while the 4+ response manifested an extensive infiltrate of this type. Neovascularization was likewise scored on a 0-4 scale with 0 denoting no vascularization and 4 denoting about 1/10 of the wound space occupied by capillaries. Although the whole sponge area was used for analysis we noted that the most striking differences between the various treatments were evident in the center of the sponge. Therefore, the histologic appearance of the central zone was selected for presentation.

A sponge containing a collagen/sucrose octasulfate composite (8.75/1.0 mg/ml) reflected granulation tissue, rich in fibroblasts and in neovascular growth. At one-tenth the concentration of sucrose octasulfate (collagen/sucrose octasulfate at 8.75/0.1 mg/ml) there was still a strong fibroblastic and neovascular response. Reducing the concentration of sucrose octasulfate in the composite to 0.01 mg/ml resulted in a marked loss of the angiogenic effect. On the other hand, injection of composite of collagen/sucrose octasulfate at 8.75/10.0 mg/ml resulted in both gross and microscopic hemorrhage.

Other compounds were tested in a similar manner. The results of these tests are set forth in Table V set forth in Example 16. Similar tests with sucralfate showed strong inflammatory response with no neovascularization or fibroblast migration.

Biochemical Analysis

Sponges were surgically removed on the seventh day after implantation and the adhering connective tissue capsule carefully removed from their surfaces. DNA content was determined by the diphenyl-amine method (Grossman L, Moldave K (eds.) *Methods in Enzymology*, Vol. 12, Part B. Academic Press, New York, pp. 163-166, 1968.) DNA synthesis was measured by the 24-hour incubation of finely minced sponges in Dulbecco's modified Eagle's medium (DMEM) supplemented with 10 percent fetal calf serum, 2 mM glutamic acid and 10 uCi/ml $^3$H-thymidine (Amersham, Arlington Heights, Ill.). At the conclusion of the incubation period the medium and an equal volume of 20 percent trichlorocetic acid (TCA) were mixed and centrifuged at 1000×g for 15 minutes at 4 degrees Centigrade. The precipitate was washed three times with 10 percent TCA, suspended in 1 M perchlorocetic acid and heated to 100 degrees Centigrade for 30 minutes. Aliquots were then combined with fluor solution (PCS, Amersham) and radioactivity measured in a liquid scintillation counter (Tricarb, Packard Instrument Co., Downer Grove, Ill.)

Assays for protein synthesis were carried out on separate sponges. The minced sponges were incubated as described above except that 1 μCi $^{14}$C-proline (Amersham) was added. After 24 hours the medium was mixed with an equal volume of 20 percent TCA and centrifuged at 1000×g for five minutes. The precipitate was digested with chromatographically purified colagenase (Worthington, Freehold, N.Y.) and $^{14}$C-proline and hydroxyproline content determined according to the method of Peterkofsky, et al. (Furthmyer H. (ed.). *Immunochemistry of the Extracellular Matrix*, Vol. II, CRC Press, Boca Raton, Fla., pp. 19-47, 1982).

Biochemical analyses of total DNA, DNA synthesis and collagen synthesis are summarized in Table I. Both the increase in total DNA and the rate of DNA synthesis confirm the histologic picture of a high degree of fibroblast infiltration. No significant change in collagen synthesis from controls was observed.

TABLE I

| Added to Sponge | DNA (ug/sponge) | DNA Synthesis (% of control) | Collagen CPM in collagen | Synthesis % of total protein synthesis |
|---|---|---|---|---|
| PBS | 14.8 ± 3.9 | 100 ± 32 | 2474 ± 281 | 9.1 ± 1.3 |
| Collagen | 21.2 ± 1.6 | 105 ± 24 | 2431 ± 457 | 8.8 ± 1.2 |
| Collagen/ Sucrose Octasulfate (8.75/1.0 mg/ | 37.1 ± 4.9 | 186 ± 39 | 3192 ± 741 | 9.4 ± 1.6 |

TABLE I-continued

| Added to Sponge ml) | DNA (ug/sponge sponge) | DNA Synthesis (% of control) | Collagen CPM in collagen | Synthesis % of total protein synthesis |
|---|---|---|---|---|

The rate and extent of fibroplasia and neovascularization induced by the collagen/sucrose octasulfate composite is remarkable. At the ratios of 8.75/1.0 and 8.75/0.1 mg/ml granulation tissue that was extremely rich in fibroblasts and capillaries formed within seven days. Control sponges injected with phosphate buffer saline or with collagen only showed only sparse cellular infiltration and very poor neovascular response. Composites that contained 10.0 mg/ml sucrose octasulfate caused a local hemorrhagic response. On the other hand, 0.01 mg/ml sucrose octasulfate in the composites showed only little enhancement of repair.

Effect of Sucrose Octasulfate Encapsulated in Hydron

Impregnation of sponges with sucrose octasulfate encapsulated in Hydron gave similar results to those obtained by collagen/sucrose octasulfate composites. Thus, injection of 50 uL of Hydron containing either 1.0 mg/ml or 0.1 mg/ml sucrose octasulfate caused the formation of granulation tissue densely populated with fibroblasts and highly vascularized with new capillary growth. As in sponges impregnated with collagen/sucrose octasulfate at 8.75/10.0 mg/ml, 10.0 mg/ml of sucrose octasulfate in Hydron caused local hemorrhage.

The fact that addition of sucrose octasulfate in Hydron, without the addition of collagen, yielded similar results to those obtained by addition of collagen/sucrose octasulfate sponge composites may be interpreted in several ways. It may indicate that the sole function of collagen is to allow the slow release of sucrose octasulfate. Alternatively, sucrose octasulfate may interact with either the exogenously added or endogenously synthesized collagen so as to create a fibrillar array conducive to fibroblast and endothelial cell infiltration.

Example 14

Effect of Sucrose Octasulfate on Repair of Bone Fractures

Another model system of repair is that of bone fracture, but unlike the sponge implantation site, the former is identical in all respects to the clinical situation.

The ulnae of 18 guinea pigs were exposed surgically and then fractured at the midshaft, using a very fine dental burr as a saw. The intact radius served as an immobilization splint. The animals were divided into six groups, three in each, according to the treatment at the fracture site, which was as follows:
Group 1. Untreated controls
Group 2. Sucrose octasulfate 1.0 mg/ml instilled at the fracture site with a syringe
Group 3. Sucrose octasulfate 4.0 mg/ml
Group 4. Collagen (a native 0.25% neutral salt solution)
Group 5. Collagen plus sucrose octasulfate 1.0 mg/ml
Group 6. Collagen plus sucrose octasulfate 4.0 mg/ml The animals were sacrificed ten days after surgery, and the fractured bones were dissected and processed for both histologic and biochemical analyses.

The results showed unequivocally that fractures treated with collagen plus sucrose octasulfate 1.0 mg/ml were at a conspicuously advanced stage of healing compared to either the untreated controls or to any other mode of treatment. This was manifested by relatively more peri- and endosteal new bone, distinct remodeling, and the complete absence of fibrin, which was still present in the other groups (indicating an earlier stage of healing). Biochemically, a significant relative increase in mineralization was the most important finding, concomitant with a decrease in both DNA and hydroxyproline per milligram of tissue. When the percent loss of minerals following decalcification of the fractured bones was calculated the highest percentage (77%) was found in the collagen/sucrose octasulfate 1.0 mg/ml-treated fractures.

TABLE II

| | before decalcification | before decalcification | decrease mg | decrease % |
|---|---|---|---|---|
| untreated control | 4.90 | 2.40 | 2.50 | 51.0 |
| collagen | 5.50 | 2.10 | 3.40 | 61.8 |
| sucrose octasulfate (1 mg/ml) | 7.00 | 2.20 | 4.80 | 68.6 |
| sucrose octasulfate (4 mg/ml) | 5.90 | 2.60 | 3.30 | 55.9 |
| collagen + sucrose octasulfate (1 mg/ml) | 9.30 | 2.05 | 7.25 | 77.9 |
| collagen + sucrose octasulfate (4 mg/ml) | 6.07 | 2.07 | 4.00 | 65.9 |

As shown above collagen/sucrose octasulfate composites induced both endosteal and periosteal new bone formation within ten days. Normally such fractures still contain fibrin and necrotic tissue and no new bone is formed. To our knowledge such an early onset and vigorous repair process has not been reported.

Example 15

Rabbit Cornea Assay for Angiogenesis

Sucrose octasulfate proved to be extremely angiogenic, as shown by the rabbit cornea assay. This may offer an explanation for the dense vascular bed that characterized the granulation tissue in the in-vivo experiments. Sucrose octasulfate at concentrations of 0.1 to 100 ug/ml was encapsulated in Hydron and implanted in rabbit corneas. The method used was that described in Surgery 96:48-54, 1984. The test solution (sucrose octasulfate or PBS) was mixed with an equal volume of Hydron and allowed to polymerize under reduced pressure. Pellets of Hydron-encapsulated test material were implanted in pockets created in the corneas 2-mm proximal to the superior limbus. Eyes were evaluated at days 1 through 14 post-implantation for gross inflammation and, as described by Hunt, et al. in Surgery 96:48-54, 1984, for angiogenesis. Corneal neovascularization was graded on a scale of 0-4+ (integers only being assigned). Zero denotes a normal eye with no ingrowth on limbal vessels into the corneal stroma; 1+, up to 1 mm of capillary ingrowth in a localized arc adjacent to the injection site; 2+, 1-2 mm ingrowth; 3+, 2-3 mm ingrowth; and 4+, 3 mm or greater ingrowth in a wide arc along the limbal edge toward the injection site. Eyes that demonstrated positive angiogenesis were removed, fixed and stained with hematoxylin and losin (H&E). To ascertain that the observed angiogenesis was not secondary to an inflammatory process some eyes with a positive response were removed and stained with H&E and a nonspecific esterase stain as early as two days after implantation.

Implantation of 10 and 100 μg/ml gave the most potent angiogenic response. The extent of angioqenesis decreased in response to lower concentrations of sucrose octasulfate (1.0 μg/ml) and was negative at a concentration of 0.1 ug/ml. Table III sets forth the results of the assay.

TABLE III

| Conc. | No. Corneas Implanted | No. Positive Responses |
|---|---|---|
| 100 ug/ml | 9 | 8 |
| 10 ug/ml | 5 | 4 |
| 1 ug/ml | 6 | 1 |
| 0.1 ug/ml | 5 | 0 |

Results of the angiogenesis test for various compounds of the invention are set forth in Table V in Example 16.

Example 16

Cell Migration Assay

The Boyden chamber assay shows that sucrose octasulfate stimulates fibroblast movement, which could account for the heavy fibroblast migration that was observed histologically. Stimulation of directed movement of fibroblasts was assayed as described by Banda M. J., Knighton D. R., Hunt T. K., Werb A., Isolation of a nonmitogenic angiogenesis factor from wound fluid, Proc. Natl. Acad. Sci. 79:7773–7777, 1982. Briefly, solutions of sucrose octasulfate in PBS in concentrations resulting in final concentrations ranging from $10^{-2}$ to $10^{-7}$ g/ml diluted to a final volume of 300 μL in DMEM supplemented with 10 percent platelet-poor rabbit serum were placed in the bottom of Boyden blind-well chambers. Polylysine-coated, 5 μ-pore diameter, polycarbonate filters (Nucleopore) were placed over the test solution and $1.75–3.0 \times 10^6$ fibroblasts suspended in DMEM added to the top compartment. The chambers were incubated for two and a half hours at 37 degrees Centigrade. At the end of incubation the top filters was fixed, stained and evaluated by counting the number of cells that had migrated to the bottom side of the filter. For each experiment five random fields per filter and at least 15 filters per each concentration of sucrose octasulfate were conducted. Table IV summarizes the results.

TABLE IV

| Sucrose Octasulfate Concentration (g/ml) | Cell/High Power Field (fold increase over negative control) |
|---|---|
| 10 −2 | 0.4 |
| 10 −3 | 0.4 |
| 10 −4 | 0.6 |
| 10 −5 | 2.2 |
| 10 −6 | 2.1 |
| 10 −7 | 1.1 |

The results indicate that $10^{-5}$ to $10^{-7}$ g/ml sucrose octasulfate caused movement of cells along a chemical gradient.

Results of the cell migration assay in the Boyden chamber for various compounds of the invention are set forth below in Table V. The same compounds were synthesized as set forth in Examples 1 to 12. Several were purchased from commercial sources. In particular, potassium dextran sulfate, high MW and potassium D-glucose-6-sulfate (Sigma Chem. Co., St. Louis, Mo.), potassium dextran sulfate, low MW (Calbiochem-Behring, Div. of American Hoescht Corp., La Jolla, Calif) and sodium cellulose sulfate (Aldrich Chemical Company, Inc. Milwaukee, Wis.).

TABLE V

| Compound (Potassium Salts) | Sponge | Angiogenesis | Chemo-inesis |
|---|---|---|---|
| Sucrose Octasulfate | 4 | 4 | 4 |
| Maltose Octasulfate | 3.0 | 3.0 | 3.0 |
| Trehalose Octasulfate | 3.0 | 3.0 | 2.0 |
| Beta-Lactose Octasulfate | 3.0 | 3.0 | 3.0 |
| Melezitose Undecasulfate | 1 | 1 | 1 |
| Stachyose Tetradecasulfate | 2.5 | 2.5 | 2.0 |
| Sucrose Penta/Hexasulfate | 3.5 | 3.0 | 3.0 |
| Sucrose Trisulfate | 2.5 | 2.0 | 3.0 |
| Mannose Pentasulfate | 3.0 | 3.0 | 4.0 |
| Glucose-6-Sulfate | 1 | 1 | 1 |
| Glucose Pentasulfate | 2.5 | 2.0 | 3.0 |
| Cellulose Persulfate | 1 | 1 | 1 |
| Dextran Sulfate (High MW) | 1 | 1 | 1 |
| Dextran Sulfate (Low MW) | 1 | 1 | 1 |

Based on the foregoing it appears that the degree of sulfation is important for wound healing with significant effects being observed when three or more sulfate groups are present. Optimum results appear to be achieved with persulfation. Similarly the sugar moiety and the number of sugars also affect the degree of wound healing activity. Mono- and disaccharides showed good activity provided adequate sulfate groups were present in the molecule.

Example 17

Sucrose Octasulfate Induced Collagen Fibrillogenesis

Sucrose octasulfate-induced collagen fibril formation was studied in a spectrophotometer equipped with a stopped-flow apparatus. Sucrose octasulfate at concentrations ranging up to 0.2 mg/ml was mixed with 0.5 mg/ml collagen at pH 7.4, and turbidity was monitored at 450 mμ at predetermined time intervals.

The interaction between sucrose octasulafe (0.2 mg/ml) and collagen (0.5 mg/ml) resulted in the rapid (60–70 msec) formation of collagen fibrils. The critical concentration of sucrose octasulfate, namely, the lower concentration required for initiation of fibrilloqenesis of collagen (a concentration of 0.5 mg/ml) was 0.01 mg/ml. At this concentration fibrillogenesis was initiated, but the complex was transient and dissociated within 100 msec. Protamine sulfate (0.5 mg/ml), a specific inhibiter of heparin, caused about 90 percent inhibition of the reaction between sucrose octasulfate (0.2 mg/ml) and collagen.

The foregoing experiment was repeated with the sucrose octasulfate and collagen being permitted to react at pH 3.0. Identical results were obtained.

The foregoing provides conclusive evidence that sucrose octasulfate indeed interacts with collagen and thereby induces rapid changes in the latter's organizational state. The reaction is rapid (60–75 msec) and results in the formation of typical collagen fibrils observed in the electron microscope. Furthermore, the fact that the reaction could be initiated by five moles of sucrose octasulfate per mole of collagen indicates that specific interaction is involved. The alternative hypothesis, namely that fibril formation was driven by charge neutralization, is less plausible because the reaction proceeded at pH 7.4. That hypothesis is also less plausible when the size of the collagen molecule (MW 300,000, 1000 residues per polypeptide chain) relative to sucrose octasulfate is considered.

Example 18

Clinical Assessment of Sucrose Octasulfate

Five patients were subjected to a dose-response trial using sucrose octasulfate in water. The test was a double-blind trial with four treatment arms, 0.1, 1.0, or 10 mg/ml or placebo (sterile water for irrigation). Patients were entered following debridement of the study pressure ulcer and a gauze sponge was saturated with sucrose octasulfate solution (i.e. sucrose octasulfate in sterile water vehicle) or placebo and packed into the ulcer crater, then covered with biobrane dressing to keep the area moist. Treatments were applied twice daily for a 30 day interval for four patients and for three weeks for the fifth patient.

The patient population was bedridden comatose adults with chronic ulcers having failed with some form of previous treatment(s). The patients were kept on the same ward as they had been during months prior to the trials so nursing care was uniform prior to and during the study. Thus, any response is favorable. The first four cases are nearly uniform in that three of four treatment ulcers were trochanteric.

Specifically, the investigators observed a decrease in ulcer depth rather than surface area which is consistent with healing in light of the theory that ulcers heal from the crater up rather than contracting at the wound edges. They opined that there was healthy granulating tissue in patients 001–003. However, the results in patient 001 were not as favorable as in the others since the ulcer was undermined and it was not possible to directly apply the material to the ulcer surfaces. 004 showed no response to treatment. They were more impressed with the response in 002 and 003 than 001. Results in patient 005 were enormously impressive. Ulcer depth had decreased from 2.8 cm prestudy to 1.6 cm after 3 weeks of treatment.

Only ulcer depth and volume changed with therapy. The investigators had procedural problems with determination of volume so only the depth is used as a criterion of activity for analysis of these patients. No ulcers completely healed (closed). The investigators stated that the regenerated tissue was good, healthy, pink tissue. Depth results were as follows:

TABLE VI

| Patient | Dose | Results | Depth | Depth |
|---|---|---|---|---|
| 001 | 10 mg/ml | no reduction in ulcer depth | 0.5 cm | 0.5 cm |
| 002 | 1 mg/ml | reduction in ulcer depth | 3.0 cm | 1.5 cm |
| 003 | 0.1 mg/ml | some reduction in ulcer depth | 0.5 cm | 0.3 cm |
| 004 | placebo | no reduction in ulcer depth | 1.8 cm | 1.6 cm |
| 005 | 10 mg/ml | reduction in ulcer depth | 2.8 cm | 1.6 cm |

What is claimed is:

1. A method for promoting wound healing comprising topically applying to a wound an effective amount of a compound selected from the group consisting of synthetic polysulfated monosaccharides and oligosaccharides and their pharmaceutically acceptable salts in a pharmaceutically acceptable carrier.

2. The method of claim 1 wherein the oligosaccharide contains three or more sulfate groups.

3. The method of claim 1 wherein the compound is a disaccharide or monosaccharide.

4. The method of claim 1 wherein the oligosaccharide is persulfated.

5. The method of claim 3 wherein the disaccharide is sucrose.

6. The method of claim 1 wherein the polysulfated oligosaccharide is sucrose octasulfate.

7. The method of claim 1 or 6 wherein the salt is an alkali metal salt.

8. The method of claim 1 or 6 wherein the salt is a potassium or sodium salt.

9. The method of claim 1 wherein the oligosaccharide is applied in a liquid form.

10. The method of claim 9 wherein the liquid is water.

11. The method of claim 9 wherein the liquid is isotonic salt solution.

12. The method of claim 9 wherein the oligosaccharide is present at a concentration of 0.1 to 1.0 mg/ml.

13. The method of claim 9 wherein sucrose octasulfate is present at a concentration of 0.28 mg/ml.

14. The method of claim 1 wherein the oligosaccharide is applied in combination with collagen.

15. The method of claim 14 wherein the combination of collagen and oligosaccharide is applied as a liquid suspension.

16. The method of claim 15 wherein the suspension contains 2 to 15 mg/ml collagen.

17. The method of claim 16 wherein the suspension comprises 0.28 mg/ml sucrose octasulfate and 8.75 mg/ml collagen suspended in an isotonic salt solution.

18. The method of claim 1 wherein the oligosaccharide is encapsulated in a polymer or other carrier which is capable of effecting sustained release of the oligosaccharide.

19. The method of claim 1 wherein healing of skin or bone wounds is promoted.

20. The method of claim 1 wherein the compound is applied to a wound in a bone.

21. A method of promoting wound healing by means of neovascularization and fibroblast migration comprising topically applying to a wound an effective amount of a compound selected from the group consisting of synthetic polysulfated monosaccharides and oligosaccharides and their pharmaceutically acceptable salts in a pharmaceutically acceptable carrier.

* * * * *